(12) United States Patent
Snyder et al.

(10) Patent No.: US 7,393,526 B2
(45) Date of Patent: Jul. 1, 2008

(54) SYSTEMIC GENE DELIVERY VEHICLES FOR THE TREATMENT OF TUMORS

(75) Inventors: Evan Y. Snyder, Jamaica Plain, MA (US); Karen S. Aboody, Needham, MA (US); Alice B. Brown, Boston, MA (US); Xandra O. Breakefield, Newton Center, MA (US)

(73) Assignee: Children's Medical Center Corporation, Boston, MA (US)

( * ) Notice: Subject to any disclaimer, the term of this patent is extended or adjusted under 35 U.S.C. 154(b) by 208 days.

(21) Appl. No.: 10/204,160

(22) PCT Filed: Mar. 15, 2001

(86) PCT No.: PCT/US01/08273

§ 371 (c)(1), (2), (4) Date: Nov. 5, 2003

(87) PCT Pub. No.: WO01/68148

PCT Pub. Date: Sep. 20, 2001

(65) Prior Publication Data

US 2005/0019313 A1  Jan. 27, 2005

Related U.S. Application Data

(60) Provisional application No. 60/189,720, filed on Mar. 15, 2000.

(51) Int. Cl.
*A61K 48/00* (2006.01)

(52) U.S. Cl. .................. 424/93.21; 424/93.1; 424/93.2

(58) Field of Classification Search ........................ None
See application file for complete search history.

(56) References Cited

U.S. PATENT DOCUMENTS

| | | | |
|---|---|---|---|
| 5,624,830 A | 4/1997 | Mullen et al. | |
| 5,750,376 A | 5/1998 | Weiss et al. | |
| 5,753,506 A | 5/1998 | Johe | |
| 5,851,832 A | 12/1998 | Weiss et al. | |
| 5,958,767 A * | 9/1999 | Snyder et al. | 435/368 |
| 6,497,872 B1 * | 12/2002 | Weiss et al. | 424/93.1 |
| 6,528,306 B1 * | 3/2003 | Snyder et al. | 435/368 |
| 6,541,255 B1 * | 4/2003 | Snyder et al. | 435/368 |
| 6,680,198 B1 * | 1/2004 | Snyder et al. | 435/368 |
| 6,749,850 B1 * | 6/2004 | Finkelstein et al. | 424/93.7 |

FOREIGN PATENT DOCUMENTS

WO  WO 00/20560 A1  4/2000

OTHER PUBLICATIONS

Cowan et al, Clin Cancer Res 1999;5:1619-28.*
Garcia-Sanchz et al, Blood 1998;92:672-82.*
Zhao et al, Blood 1997;90:4687-98.*
Game et al, Wien Klin Wochenschr 2001;113:832-38.*
Platt et al, Nat Biotech Mar. 2002;231-2.*
Aboody, K.S. et al., "Neural stem cells display extensive tropism for pathology in adult brain: evidence from intracranial gliomas," Proc. Natl. Acad. Sci. USA, 97:12846-12851, (Nov. 7, 2000).
Benedetti, S. et al., "Gene Therapy of Experimental Brain Tumors Using Neural Progenitor Cells," Nature Medicine, 6(4):447-450, (Apr. 2000).
Black, P., "Chapter 18: Meningiomas," Cancer of the Nervous System, Blackwell Scientific Inc. (Boston), p. 349-362. (Nov. 1996).
Brüstle, O., "Chimeric brains generated by intraventricular transplantation of fetal human brain cells into embryonic rats," Nature Biotechnology, 16:1040-1044, (Nov. 1998).
Culver, K.W. et al., "In Vivo Gene Transfer with Retroviral Vector-Producer Cells for Treatment of Experimental Brain Tumors," Science, 256:1550-1552, (Jun. 12, 1992).
Flax, J.D. et al., "Engraftable human neural stem cells respond to developmental cues, replace neurons, and express foreign genes," Nature Biotechnology, 16:1033-1039, (Nov. 1998).
Kramm, C.M. et al., "Gene Therapy for Brain Tumors," Brain Pathology, 5:345-381, (1995).
Lal, B. et al., "Endothelial cell implantation and survival within experimental gliomas," Proc. Natl. Acad. Sci. USA, 91:9695-9699, (Oct. 1994).
Ojeifo, J.O. et al., "Angiogenesis-directed Implantation of Genetically Modified Endothelial Cells in Mice," Cancer Research, 55:2240-2244, (Jun. 1, 1995).
Short, M.P. et al., "Rapid Communication Gene Delivery to Glioma Cells in Rat Brain by Grafting of a Retrovirus Packaging Cell Line," Journal of Neuroscience Research, 27:427-439, (1990).
Snyder, E.Y. et al., "Multipotent Neural Progenitor or Stem-like Cells May Be Uniquely Suited for Therapy for Some Neurodegenerative Conditions," Clinical Neuroscience, 3:310-316, (1996).
Svendsen, C.N., "Review Article: Neural Stem Cells for Brain Repair," Alzheimer's Research, 3(4):131-135, (Aug. 1997).
Tamura, M. et al., "Targeted Killing of Migrating Glioma Cells by Injection of HTK-Modified Glioma Cells," Human Gene Therapy, 8:381-391, (Mar. 1, 1997).
Noble, M., "Can neural stem cells be used to track down and destroy migratory brain tumor cells while also providng a means fo repairing tumor associated damage?," Proc. Natl. Acad. Sci. USA , 97(23):12393-12395, (Nov. 7, 2000).

* cited by examiner

*Primary Examiner*—Q. Janice Li
(74) *Attorney, Agent, or Firm*—Nixon Peabody LLP

(57) ABSTRACT

The present invention relates to the field of cellular and molecular therapy with modified (genetically or growth factor engineered) and unmodified stem cells (SCs). More particularly, the invention relates to a method of systemic treatment of central nervous system (CNS) and other tumors in both intracranial/intraspinal and extracranial/extraspinal sites, using neural stem cells (NSCs), a prototype for solid organ, non-hematopoietic stem cells.

11 Claims, 6 Drawing Sheets

SYSTEMIC GENE DELIVERY VEHICLES FOR THE TREATMENT OF TUMORS

CROSS-REFERENCE TO RELATED APPLICATIONS

This application is a National Phase Entry Application of International Application PCT/US01/08273 filed on 15 Mar. 2001 which designated the U.S and which claims the benefit of U.S. Provisional Application 60/189,720 filed 15 Mar. 2000.

FIELD OF THE INVENTION

The present invention relates to the field of cellular and molecular therapy with modified (genetically or growth factor engineered) and unmodified stem cells (SCs). More particularly, the invention relates to a method of systemic treatment of central nervous system (CNS) and other tumors in both intracranial/intraspinal and extracranial/extraspinal sites, using neural stem cells (NSCs), a prototype for solid organ, non-hematopoietic stem cells.

BACKGROUND OF THE INVENTION

Metastatic tumors present the most difficult challenge for all therapeutic approaches because of their extensive infiltration and broadcasting of the invasive tumor cells, particularly into the nervous system where they may occupy multiple locations. An eradication of more than 90% of some tumor masses may be accomplished by surgery and subsequent radiotherapy, but relapse invariably follows within months if infiltrating and metastatic cells have not been eliminated.

A number of approaches has been suggested to target and destroy the metastatic cells. One possible method is by cell-mediated vector delivery using retrovirus packaging cells to distribute retroviral vectors on site within brain tumors [Short et al., *J. Neurosci. Res.* 27, 427-439, 1990; Culver et al., *Science* 256, 1550-52, 1992; for review, see Kramm et al., *Brain Pathol.* 5, 345-381, 1995]. However, in most studies these packaging cells are derived from fibroblasts that do not migrate in the brain. In addition to fibroblasts, glioma cells [Tamura et al., *Hum Gene Ther* 8, 381-9, 1997] and endothelial cells [Lal et al., *Proc Natl Acad Sci USA* 91, 9695-9, 1994; Ojeifo et al., *Cancer Res* 55, 2240-44, 1995] have been used as vehicles to migrate throughout a tumor. A major disadvantage of using glioma cell as vehicles is that they themselves are tumorigenic and hence could contribute to the tumor burden. Endothelial cells can migrate within a glioma and are non-tumorigenic, but they have not been observed to move beyond the main tumor mass to target metastatic tumor cells or to "home in" on tumors from a distant source [Ojeifo et al., *Cancer Res* 55, 2240-44, 1995; Lal et al., *Proc Natl Acad Sci USA* 91].

The requirement for cells to have high migratory potential within the tumor and toward metastases without tumor formation is ideally fulfilled by neural stem cells (NSCs). NSCs are immature, uncommitted cells that give rise to the array of more specialized cells of the nervous system. They are defined by their ability to self-renew, to differentiate into cells of most (if not all) neuronal and glial lineages, and to populate developing and/or degenerating central nervous system (CNS) regions in multiple anatomical and developmental contexts. Clones of NSCs have been propagated in culture and reimplanted into mammalian brain where they have been shown to reintegrate appropriately and stably express foreign genes. One of the earliest uses of the NSCs as a therapeutic tool was delivering a missing gene product β-glucuronidase throughout the brain of a newborn mouse to correct a model of lysosomal storage disease mucopolysaccharidosis type VII [Snyder et al., *Nature*, March 1995]. In preliminary studies, NSCs have also been observed to migrate toward damaged brain regions and continue to express exogenous genes [Snyder and Macklis, *Clin Neurosci* 3, 310-16, 1996].

Most early studies of NSC biology were performed with rodent NSCs, but increasing attention has been focused on human NSCs due to their obvious clinical potential [Black and Loeffler (eds). CANCER OF THE NERVOUS SYSTEM. Blackwell Scientific Inc, Boston, 1996, pp 349-61, Flat et al., *Nature Biotech.* 11, 1998; Brustle O. et al., *Nature Biotech.* 11, 1040-49, 1998]. Several human cell lines of neural and stem cells have consequently been isolated from the human fetal telencephalon, propagated in culture, transfected with the lacZ reporter gene and cloned. Human NSCs have been demonstrated to migrate throughout the whole brain, differentiate into neurons and glia, and integrate into the neural architecture and express reporter genes after transplantation into rodent brains [Flat et al., *Nature Biotech.* 11, 1998].

It would be desirable to have a safe, efficient and convenient system for delivering therapeutic agents to intracerebral tumors, cerebral metastases from an extracerebral tumor, or other extracerebral tumors that metastasize to other organs.

SUMMARY OF THE INVENTION

The present invention is based upon a surprising finding that stem cells, for example neural stem cells (NSCs), can migrate throughout a tumor, track invading and/or metastatic tumor cells and, when administered systemically, e.g., via an intravascular route, can cross the blood brain barrier to reach tumor cells in the brain. Stem cells administered into the cerebrospinal fluid (CSF) via intracisternal, intrathecal, and intraventricular routes can similarly enter nervous system parenchyma.

We have further surprisingly discovered that modified (genetically or growth factor engineered) or unmodified NSCs target tumor cells, including metastatic tumor cells, both intracranially and extracranially, when delivered through the peripheral vasculature.

The invention provides a method to treat tumors by administering modified or unmodified stem cells, more preferably neural stem cells or stem cells directed down a neural lineage, to an individual affected by tumors.

The present invention provides a method for not only attacking the tumor proper but also for attacking and killing metastasizing cells while minimizing harm to surrounding tissue.

In one embodiment, the present invention provides a method of treating a tumor in an individual in need thereof comprising (a) providing a plurality of modified or unmodified stem cells (SCs) capable of migrating to the tumor (both in and outside the nervous system) and exerting a therapeutic effect; and (b) delivering to the individual the SCs, thereby making at least one therapeutic agent available to the tumor. In the preferred embodiment, the stem cells are administered systemically. In the most preferred embodiment, the systemic administration is performed intravascularly. For some applications, the stem cells may be administered via the CSF.

In the method of the present invention SCs can be obtained from adult, post-natal, fetal or embryonic mammalian (including human) solid tissue or organ or developmental precursor thereof Examples of suitable solid organs and tissues include but are not limited to e.g., liver, pancreas, spleen, kidney, thyroid, pituitary gland, appendix, tonsil, gut, lung, gut-associated lymphoid tissue, mucosa-associated lymphoid tissue, tongue, mucosal tissue, adrenal gland, thymus, neuronal tissue, central nervous system tissue, spinal cord, hypothalamus, bone, including osteoclasts and osteoblasts, mesanchyme, muscle, including myoblasts, myocytes, satellite cells and the like, and inner cell mass of embryo. Preferably, the SCs are neural stem cells (NSCs) or stem cells directed down a neural lineage.

The tumor can be an intracranial/intraspinal tumor, intracranial/intraspinal metastases from an extracranial/extraspinal tumor, or other extranervous system tumor.

In one embodiment, the present invention provides modified stem cells. As used herein, "modified" means that the cells are transfected, transduced or otherwise genetically engineered to deliver or express a substance that confers a therapeutic benefit. The substance is preferably encoded by a nucleic acid. The nucleic acid is preferably contained within a vector. A viral vector is preferred. In one embodiment, for example, the substance is an enzyme capable of converting non-toxic compound to a toxic compound that exerts a therapeutic effect. The modifications are not limited to genetic modifications, however, growth factors or proteins may be used to treat the SCs. Furthermore, unmodified SCs intrinsically express therapeutic agents which are useful for treatment against the tumor.

Therapeutic substances include, but are not limited to, those that result in: a) the dissemination of cytotoxic gene products, b) expression of factors that directly promote differentiation of neoplastic cells, c) release of antiangiogenic agents, and d) the more efficacious delivery of viral vector-encoded therapeutic gene products throughout the tumor (e.g., suicide genes, pro-apoptotic genes, trophin receptors).

In another embodiment, the present invention provides a method of treating a tumor in an individual in need thereof, which includes providing a preparation containing stem cells transfected to produce cytosine deaminase and injecting intravascularly the stem cell preparation. After a time sufficient to permit the stem cell to migrate to the tumor cells, 5-fluorocytosine is administered, which the stem cells convert to toxic 5-fluorouracil in the presence of the tumor cells which are killed.

In another embodiment, there is provided a kit for systemic treatment of a tumor, the kit includes a vial of frozen SCs or cells ready for implantation, the SCs having been modified and/or determined to exert a therapeutic effect on a tumor and being capable of migrating to the tumor, a container of a pharmaceutical grade solution for suspending the SCs, and an injection syringe.

BRIEF DESCRIPTION OF FIGURES

FIG. 1A: 20 mm and FIG. 1B: 15 mm.

FIG. 1C: 60 mm; FIG. 1D: 30 mm; and FIG. 1E: 15 mm. Both human and murine CD-NSCs displayed migratory characteristics similar to the non-transduced NSCs regarding tropism for experimental intracranial gliomas.

FIGS. 2A-2C summarize the significant antitumor effect of CD-expressing NSCs in vitro. CNS-1 glioblastoma cells were co-cultured with murine CD-NSCs (FIGS. 2A and 2B) or human CD-NSCs. Representative low power fields are shown after fixation and X-gal staining (CD-NSCs dark blue, tumor cells pale) three days after plating with or without 5-FC. Cell co-cultures receiving no treatment were virtually confluent (FIG. 2A); whereas, plates receiving 5-FC showed a significant reduction in tumor cells (FIG. 2B). In this treatment regime, the NSCs were still dividing and thus also subject to elimination by 5-FU and its toxic metabolites. The bar graph of FIG. 2C shows average counts of tumor cells per high-power field. Note the significant reduction in treated murine (white and sparsely dotted bars) and human CD-NSC cocultures (asterisks over SEM error bars) as compared to an untreated plates (densely dotted bar). Note also, that the tumor-killing effect was virtually identical whether 50,000 or 100,000 CD-NSCs were initially plated with 200,000 tumor cells.

FIGS. 3A through 3D illustrate that the CD-expressing NSCs produce a significant reduction in tumor mass in vivo. CNS-1 glioblastoma cells alone, or CNS-1 cells co-transplanted with human CS-NSCs were implanted into the frontal lobe of adult nude mice. Two days later, treated animals began to receive daily intraperitoneal injections of 5-FC which continued for ten days. The graph of FIG. 3A displays tumor mass expressed as a percentage of control, untreated tumor +CD-NSC at two weeks after implantation. These data were obtained by measuring tumor section, examples of which are provided in FIGS. 3B, 3C and 3D. Note that there was about an 80% reduction in tumor mass in 5-FC-treated animals transplanted with tumor and CD-NSCs (FIG. 3D). 5-FC had no effect on tumor mass in the absence of CD-NSCs (FIG. 3C). FIGS. 3B, 3C and 3D are "camera lucida" sections of tumor areas on representative cryostat tissue sections, stained with X-gal and counterstained with neutral red. Compare the large tumors in untreated tumor +CD-NSCs (FIG. 3B) and 5-FC-treated tumor alone (no CD-NSCS) (FIG. 3C) with the dramatically reduced tumors of the 5-FC-treated animals who had received both tumor and CD-NSCs (FIG. 3D).

FIGS. 4A, 4B and 4C show progressively higher power views of representative 10 μm tumor sections through the brain of an animal sacrificed 4 days following NSC tail vein injection, processed with Xgal histochemistry (FIG. 4A) and anti-βgal immunohistochemistry (FIGS. 4B and 4C) to identify donor NSCs, and counterstained with neutral red to delineate the tumor border. At low power (FIG. 4A), Xgal+ NSCs are distributed throughout the tumor, but not in surrounding normal tissue. Sister sections, reacted with a Texas red-conjugated anti-β-gal antibody and visualized at higher power (FIG. 4B) and magnified further (FIG. 4C) confirm the presence of donor-derived cells (arrow) within the tumor. Scale bar FIG. 4A: 25 μm, FIG. 4B: 20 μm, and FIG. 4C: 12 μm FIGS. 5A through 5F show that intravascularly delivered NSCs display tropism for extracranial tumors. $3-4 \times 10^6$ CNS-1 rodent glioma cells (FIGS. 5A through 5D) or SH-SY5Y human neuroblastoma cells (FIGS. 5E, 5F and 5G) were implanted subcutaneously into the flank of adult nude mice. Three weeks later, after the tumors were well established, 2-3×10⁶ C17.2 neural stem cells were injected into the tail vein. On day 4, after NSC administration, the animals were sacrificed by anesthesia overdose. FIG. 5A shows CNS-1 tumor sections stained with X-gal and NSC cells stained with neutral red. FIGS. 5B, 5C and 5D are low and high power views of sister sections processed for double immunofluorescence using a Texas red-conjugated anti-β-gal antibody for NSCs and a FITC-conjugated anti-GFP antibody for GFP-labeled glioblastoma cells. FIGS. 5E and 5F are low and high power views of SH-SY5Y tumor tissue sections stained with X-gal containing the NSC clone C17.2.CD2. FIG. 5G is a sister section of FIG. 5F processed for double immunofluorescence using a Texas red-conjugated anti-β-gal antibody for NSCs.

FIGS. 6A through 6G illustrate that intravascularly delivered NSCs display tropism for extracerebral experimental tumors within 30 minutes. 3-4×10⁶ SH-SY5Y human neuroblastoma cells were implanted subcutaneously into the left and right flank of adult nude mice. Three weeks later, when the tumors were well established, the left tumor mass was surgically removed (prior to NSC injection), and 2-3×10⁶ neural stem cells were injected into the tail vein. Approximately 30 minutes later, the animals were sacrificed by anesthesia overdose and right subcutaneous tumor mass (post-NSC injection) and organs harvested. FIGS. 6A and 6C show a low and higher power view of SH-SY5Y left flank tumor tissue sections stained with X-gal and neutral red. Note a lack of any X-gal positive cells. FIGS. 6B, 6D, 6E, 6F and 6G show a low and higher power views of SH-SY5Y right flank tumor tissue sections stained with X-gal and neutral red. Note a ring-like pattern of X-gal staining donor cells all along outer tumor border.

DETAILED DESCRIPTION OF THE INVENTION

The present invention is based upon a surprising finding that stem cells, for example neural stem cells (NSCs), can migrate throughout a tumor, track metastatic tumor cells and when administered intravenously, can cross the blood brain barrier to reach tumor cells in the brain. We have further surprisingly discovered that NSCs, including modified (genetically engineered) NSCs, target tumors, including metastatic tumor cells, both intracranially and extracranially, when delivered through the peripheral vasculature.

The invention provides a method to treat tumors by administering modified or unmodified stem cells, for example, neural stem cells, to an individual affected by tumors both inside or outside the nervous system.

The delivery method of the present invention offers a number of advantages over direct injection of virus into a tumor. For example, the virus carried by the modified stem cell can be activated after a delay to allow the cells to migrate towards metastatic tumor cells as described infra. Also, the therapeutic gene in the SCs can be driven by a tissue-specific promoter to "narrow-cast" expression of the gene to regions or cell types of concern while protecting regions that need sparing.

The stem cells useful according to the present invention include cells that are capable of migrating through a tumor, beyond a tumor/parenchyma border and brain tissue to "chase down" invading cells, or cells that can "home in" on tumors present inside and outside the nervous system from a systemic entrance point. To date, these have included not only primary brain tumors but also neuroblastoma, melanoma and prostate cancer implanted either in the brain or in the flank. They should also include any tumor cell type that metastasizes, including to the brain These stem cells can be prepared as described by Snyder [Snyder et al., *Cell* 68, 33-51, 1992; Snyder, *The Neuroscientist* 4, 408-25, 1998]. Other examples of stem cells useful according to the present invention include, but are not limited to, neural or embryonic stem cells, HSN-1 cells, fetal pig or other xenotropic cells, neural crest cells, bone marrow derived stem cells, muscle stem cells and hNT cells. The HSN-1 cells useful according to the invention can be prepared as described in, e.g., Ronnett et al., *Science* 248, 603-605, 1990. The preparation of neural crest cells is described in U.S. Pat. No. 5,654,183. The hNT cells useful according to the present invention can be prepared as described in e.g., Konubu et al., *Cell Transplant* 7, 549-558, 1998.

The stem cells according to the present invention can be modified to deliver substances that can be used to destroy or inhibit growth of tumor cells. Such substances include, but are not limited to vectors encoding genes for toxins; prodrugs; enzymes such as cytosine deaminase (CD); angiogenesis inhibitors such as TNP-470, platelet factor 4, thrombospondin-1, tissue inhibitors of metalloproteases (ITMP1 and TIMP2), prolactin (16-Kd fragment), angiostatin (38-Kd fragment of plasminogen), endostatin, bFGF soluble receptor, VEGF soluble receptor; cytokines; growth factors and their inhibitors; interleukins (IL), IL-1, IL-2, IL-3, IL-4, IL-5, IL-6, IL-7, IL-8, IL-10, and IL-11; tissue necrosis factors (TNF) TNFα and TNFβ; lymphotoxin (LT); interferons (IFN) IFNα, IFNβ and IFNγ; tissue growth factors (TGF); colony-stimulating factors (CSFs); and nerve growth factor (NGF). In the preferred embodiment, the stem cells are engineered to deliver cytocine deaminase, which converts a non-toxic 5-fluorocytosine (5-FC) into a toxic 5-fluorouridine (5-FU).

For example, the examples infra show size reduction in the experimental tumor models in the CD/5-FC prodrug example, NSCs were able to express a bioactive transgene in vivo and to effect a significant anti-tumor result 5-FU is a chemotherapeutic agent with selective toxicity to dividing cells through its toxic metabolites and can readily diffuse into surrounding tumor cells giving CD an impressive "bystander" effect. As little as 2% of the tumor mass expressing CD can generate a significant antitumor effect in response to 5-FC [Huber et al., *Proc. vatl. Acad Sci. USA* 91, 8302-06, 1994].

Vectors useful in modifying the stem cells of the invention include, but are not limited to (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picarnovirus vectors; (i) vaccinia virus vectors; (j) a helper-dependent or gutless adenovirus; and (k) lentivirus or HIV-derived vectors. In one preferred embodiment the virus is a herpes simplex type 1 virus (HSV-1). In a preferred embodiment, the vector is a replication-dependent HSV-1 vector which has been engineered to lack ribonucleotide reductase activity.

The stem cells can also be engineered to controllably express the desired substance intended to treat tumors. Such controlled expression systems include, but are not limited to drug/hormone inducible promoters, e.g., tetracycline [Gossen and Bujard, *Nucl Acids Res* 21,4411-2, 1993], rapamycin [Rivera et al., *Nat Med* 2, 1028-32, 1996], and glucocorticoid inducible promoters [Lu and Federoff, *Hum Gene Ther* 6, 419-28, 1995]; tetracycline silencer system [Freundlieb et al., *J Gene Med*. 1, 4-12, 1999], particularly combined with a "piggyback" HSV-1 delivery system [Pechan et al., *Hum Gene Ther* 7, 2003-13,1996]; and tissue specific promoters.

In one embodiment, a replication-dependent HSV-1 vector is produced by deleting the ribonucleotide reductase (RR)

gene of HSV-1 vector to render the vector susceptible to control by external expression of RR.

To avoid destruction of delivery cells by viral replication upon implantation, regulation of expression of genes by viral vectors is desired. Delayed expression allows better migration of the cells infected with a viral vector. It is preferred that the expression can be delayed for 1-6 days, preferably 3 days after the injection of the cells to avoid self-destruction of the delivery cells and to allow the stem cells to reach potential metastatic tumor cells. When using the inducible systems in viral vectors, it is important to achieve full-off baseline expression to prevent residual viral replication which can result in premature death of stem cells infected with the In one embodiment, the present invention provides stem cells, preferably neural stem cells, infected with an HSV-1 vector which has been engineered to lack the RR enzyme thereby rendering it non-replicable in the absence of externally produced RR. Because the HSV-1 vector can only replicate in dividing cells, virus replication can be regulated by regulating cell division.

Control of replication-conditional HSV-1 RR vector replication can be achieved, for example, by arresting the carrier cells growth prior to infection. For example, the drug mimosine can be used to block growth of neural stem cells at confluency and thus prevent virus replication. In addition to arresting the cell cycle in the late G1 phase, mimosine also inhibits cellular RR enzyme. Addition of mimosine in infected cells in vivo completely abolishes viral replication which is resumed after removal of mimosine. The mimosine block of cell division and viral replication is reversible at treatment times at least up to 13 days.

In another embodiment, co-treatment with ganciclovir (GCV) and mimosine as a viral replication block can be used. After GCV treatment, neural stem cells differentiate into neurons and harbor the virus in a latent state. After withdrawal of GCV and mimosine the cells need a high level of RR to allow the re-entry of the quiescent viral genome of the replication-conditional HSV-1 RR⁻ onto the replicative cycle. Alternatively, the immediate early virus proteins ICP0 or ICP4 that are known to be important in the HSV-1 re-activation can be used to re-activate the arrested viral replication [Zhu et al., $J$ $Virol$ 64, 4489-98, 1990]. In addition, viral replication proteins like ICP4 and CIP27 can also be placed under control of drug/hormone inducible promoters.

Additional genes can be inserted into the replication-dependent vector. A non-limiting example is CYP2B 1 gene, which is responsible for the bio-activation of prodrugs cyclophosphamide and ifosfamide. Once the packaging cells have migrated to the appropriate site, the appropriate prodrug can be administered to produce an oncolytic effect. Similarly, not all, the components of the tested vector are believed to be necessary. Vector constructs may additionally include a marker gene for potential histological tracking. Such markers include, but are not limited to lacZ or genes encoding fluorescent proteins such as green fluorescent protein, GFP. Genes with other functions may also be included.

In accordance with the present invention the stem cells are administered to an individual in a pharmaceutically acceptable carrier systemically. In the preferred embodiment, the stem cells are administered intravascularly, including intravenously. The stem cells may also be administered using intra-CSF or intraosseous injection. The tumor treatment method of the present invention may also be combined with traditional therapeutic interventions such as surgery, chemotherapy, radiotherapy or even other gene therapy. The cells can be administered to an individual before, during or after other treatments.

The practice of the present invention will employ, unless otherwise indicated, conventional techniques of cell biology, cell culture, molecular biology, transgenic biology, microbiology, recombinant DNA and immunology, which are within the skill of the art. Such techniques are described in the literature. [See, for example, MOLECULAR CLONING: A LABORATORY MANUAL, 2d ed. Ed. by Sambrook Fritsch and Maniatis Cold Spring Harbor Laboratory Press. 1989; DNA CLONING: VOLUMES I AND II. Ed. by D. N. Glover, 1985; OLIGONUCLEOTIDE SYNTHESIS. Ed. by M. J. Gait, 1984; Mullis et al., U.S. Pat. No. 4,683,195; NUCLEIC ACID HYBRIDIZATION. Ed. by B. D. Hames and S. J. Higgins, 1984; TRANSCRIPTION AND TRANSLATION. Ed. by B. D. Hames and S. J. Higgins, 1984; CULTURE OF ANIMAL CELLS Ed by R. I. Freshney, Alan R. Liss, Inc., 1987; IMMOBILIZED CELLS AND ENZYMES, IRL Press, 1986; PRACTICAL GUIDE TO MOLECULAR CLONING, B. Perbal, 1984; GENE TRANSFER VECTORS FOR MAMMALIAN CELLS, Ed by J. H. Miller and M. P. Calos, Cold Spring Harbor Laboratory, 1987; METHODS IN ENZYMOLOGY: VOLS. 154 AND 155, Ed. by Wu et al.; IMMUNNOCHEMICAL METHODS IN CELL AND MOLECULAR BIOLOGY, Ed. by Mayer and Walker, Academic Press, London, 1987; HANDBOOK OF EXPERIMENTAL IMMUNOLOGY: VOLS. I-IV, Ed. by D. M. Weir and C. C. Blackwell, 1986; MANIPULATING THE MOUSE EMBRYO, Cold Spring Harbor Laboratory Press, Cold Spring Harbor, N.Y., 1986].

The references cited throughout the specification are herein incorporated in their entirety. The present invention is further illustrated by the following examples and claims. The examples are provided to aid in the understanding of the invention and are not to be construed as a limitation thereof.

EXAMPLES

Example 1

CD-expressing NSCs Retain Tropism for Intracranial Glioma

Several NSC lines, both human and murine, were transduced with a transgene encoding the bacterial pro-drug activating enzyme cytosine deaminase (CD) to determine if they retained their migratory, tumor-tracking properties. On day 0, adult CD-1 mice received stereotactically guided injections of CNS-1 cells ($8 \times 10^4$ in 2 μl PBS) into the right frontal lobe, as described above, and murine or human CD-NSCs ($8 \times 10^4$ in 2 μl PBS) into the left frontal lobe; Animals received daily injections of cyclosporine 10 μg/g) and were sacrificed on Day 7. The CD-transfected donor NSCs migrated across the corpus callosum and infiltrated the tumor in adult rodents.

As shown in FIGS. 1 A and 1 B, human CD-NSCs were found distributed throughout the tumor on the opposite hemisphere at day 7 after injection. These data support the premise that both murine and human NSCs modified to express a therapeutic bioactive agent (CD) behave in a similar migratory manner to unmodified NSCs; in other words, placing in a therapeutic gene does not blunt their migratory ability.

Figure 1A:
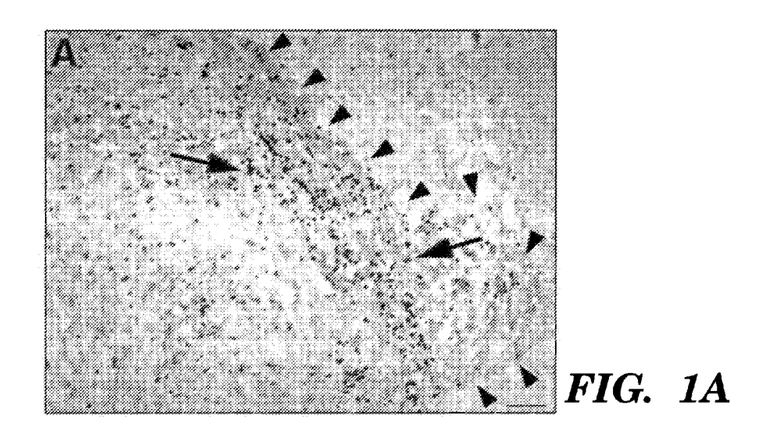
FIGS. 1A and 1B illustrate that NSCs transduced with cytosine deaminase (CD) retain tumor tracking characteristics of LacZ expressing NSCs. CNS-1 glioma cells and NSCs transduced with CD were implanted into opposite hemispheres in adult CD-1 mice, and sacrificed 7 days later. Tissue sections showing high power views of CD-transduced human NSCs (see arrows) having successfully migrated across from the other side of the brain to distribute throughout the main tumor mass (outlined by arrowheads). Sections were co-stained with human specific nuclear mitotic antibody (NSCs dark brown) and neutral red (tumor cells dark red). Scale bars.
Figure 1B:
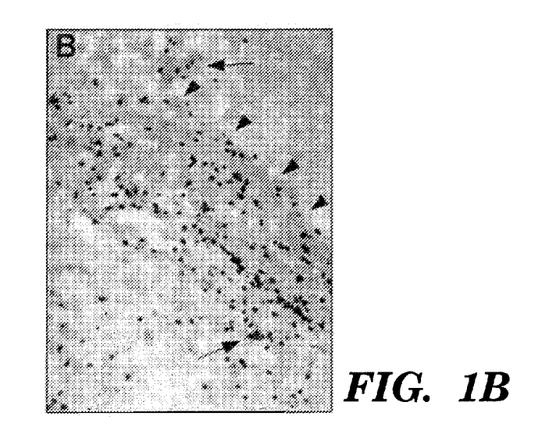
Figure 1C:
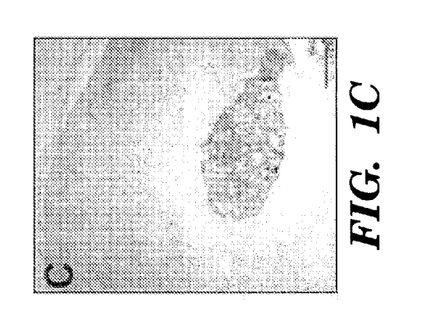
FIGS. 1C, 1D and 1E illustrate human HGL21 glioblastoma cells and hNSCs implanted into opposite hemispheres of an adult nude mouse. Pictured at progressively higher power are sections through the neutral red-stained tumor (outlined by arrowheads) intermixed with lacZ-expressing hNSCs (Xgal+blue) that migrated from the contralateral side. Scale bars.
Figure 1D:
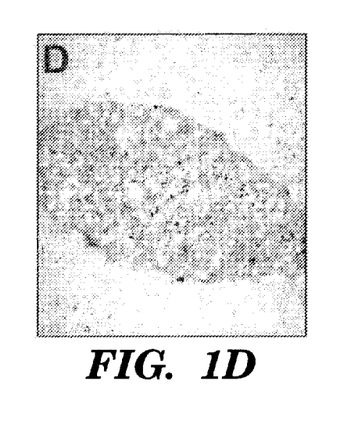
Figure 1E:
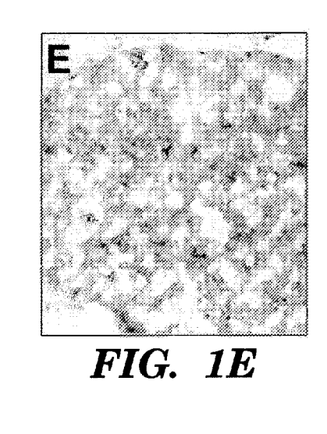

That human NSCs could similarly target a true human glioblastoma is suggested in FIGS. 1C, 1D and 1E in which primary human NSCs implanted contralateral to an HGL21-derived tumor (human GBM) established in the nude mouse cerebrum. Again, human NSCs migrated from one hemisphere to the other to populate the glioblastoma

Example 2

+CD-Expressing NSCs Produce Anti-Tumor Effect in Vitro

This experiment was performed to determine if modified CD-NSCs could effectively deliver therapy to tumor cells and produce a profound antitumor response. 200,000 CNS-1 glioma cells were plated into 10 cm Petri dishes. The following day (Day 1) media were replaced, and 50,000 or 100,000 CD-NSCs were added. On Day 2, media were replaced and 5-FC added (500 µg/ml). Control dishes included tumor-NSC co-cultures with no 5-FC treatment and tumor cell-only dishes with 5-FC treatment. Three days later, all plates were rinsed well with 1× PBS and fixed with 4% paraformaldehyde for 10 min at room temperature. Plates were stained with X-gal at 37° C. overnight to visualize NSCs and counterstained with neutral red to visualize tumor cells. Under high power, the numbers of tumor cells per field were counted. The tumor cell total was averaged from 20 random fields per plate. Error bars represent standard error of the mean.

These cell culture studies indicated significant oncolytic effects of CD-NSCs on surrounding brain tumor cells when exposed to the prodrug 5-FC. To provide proof-of-principle for therapeutic efficacy, NSCs were stably transduced with a transgene encoding the enzyme CD. CD converts the non-toxic prodrug 5-FC to the oncolytic drug 5-fluorouracil, a chemotherapeutic agent that readily diffuses into tumor cells and has selective toxicity to rapidly dividing cells.

Figures 2A, 2B:
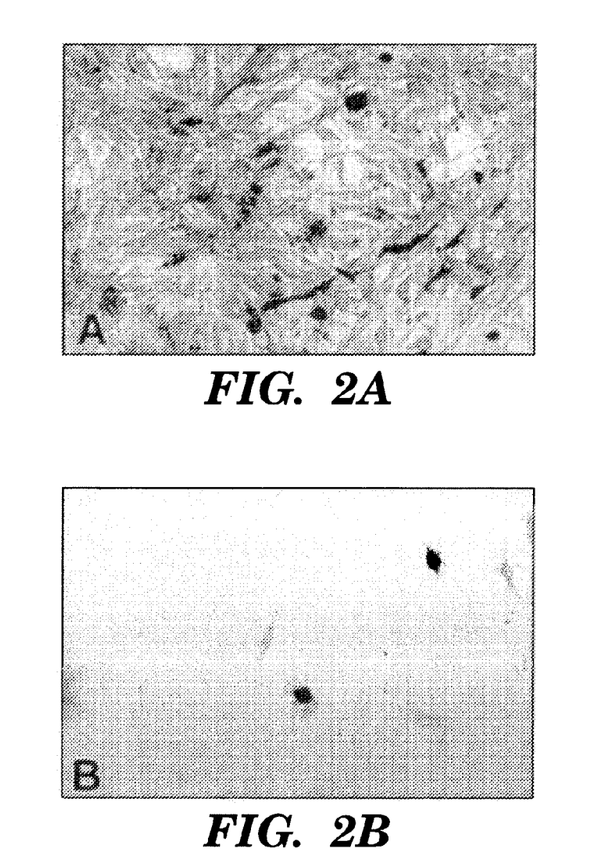
Figure 2C:
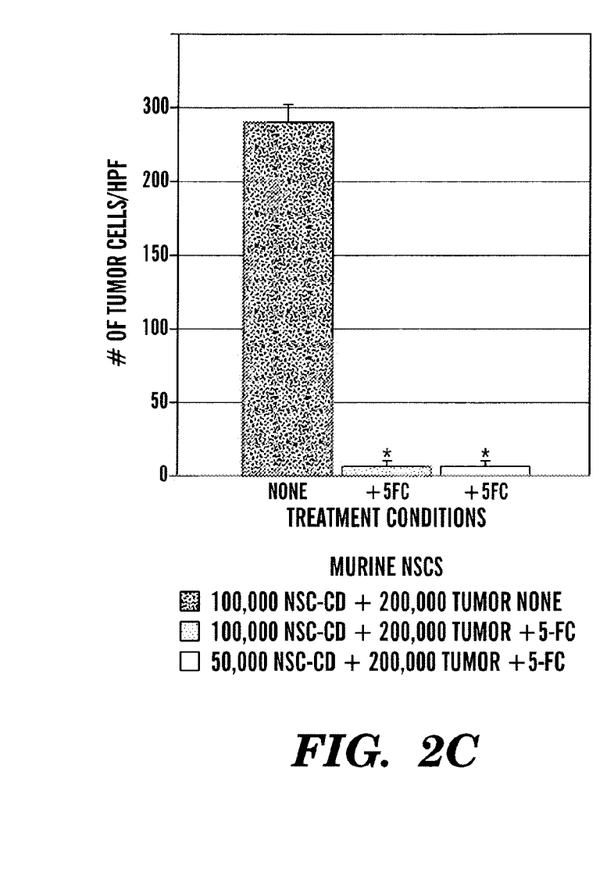
Figure 3A:
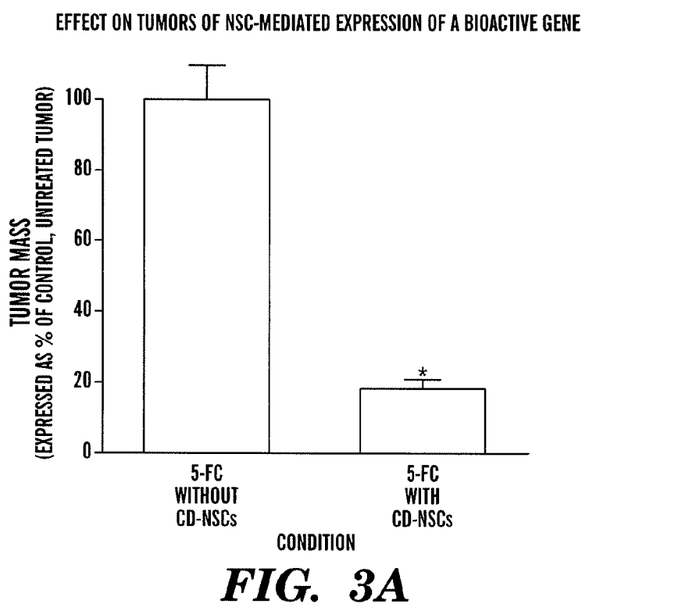
Figure 3B:
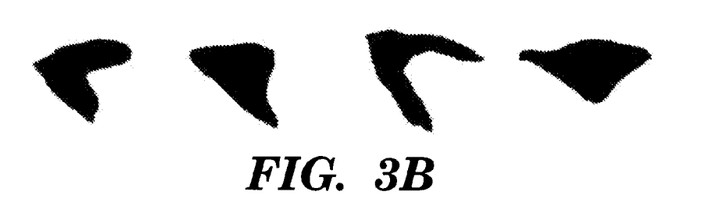
Figure 3C:
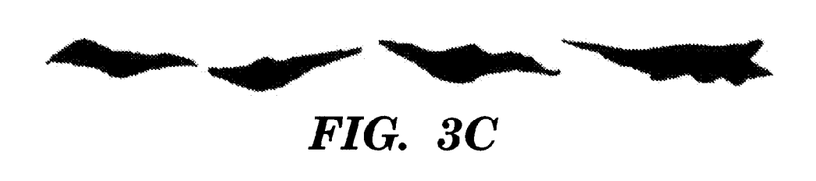
Figure 3D:
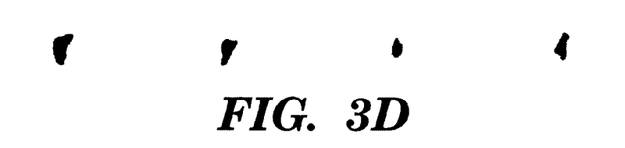
Figure 4A:
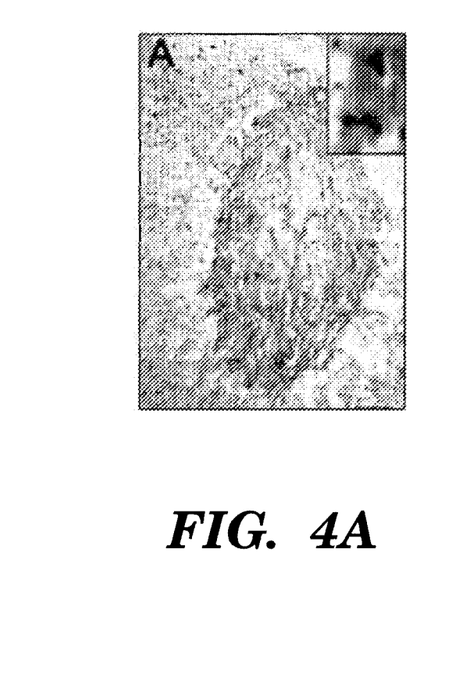
FIGS. 4A, 4B and 4C illustrate that intravascularly delivered NSCs display tropism for intracranial experimental glioma.
Figure 4B:
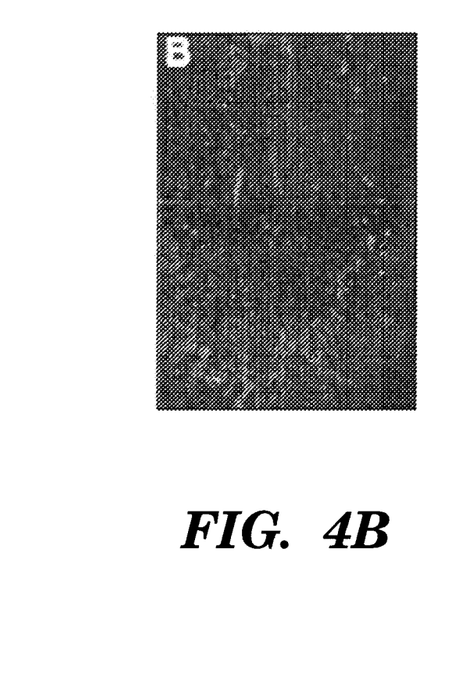
Figure 4C:
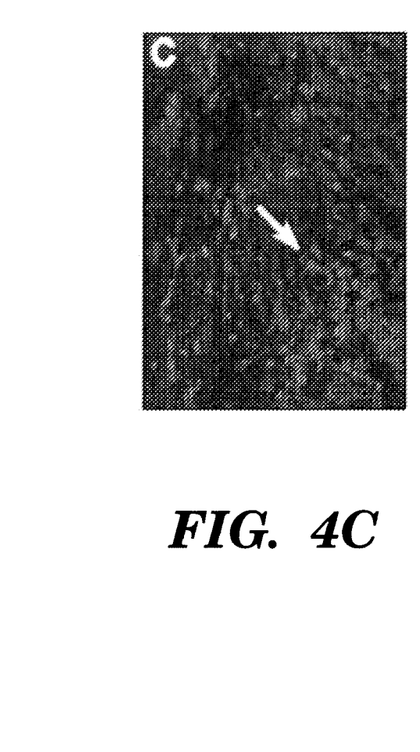
Figure 5A:
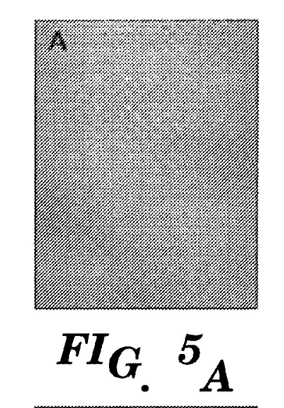
Figure 5B:
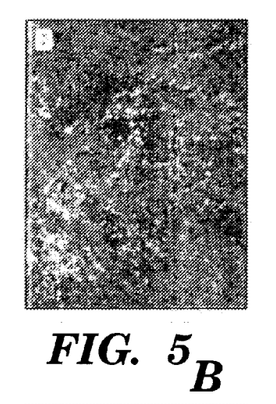
Figure 5C:
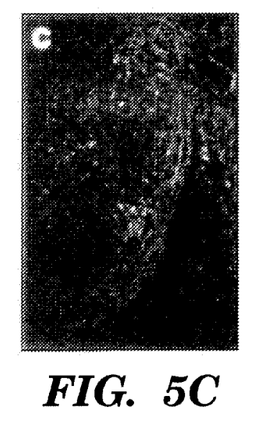
Figure 5D:
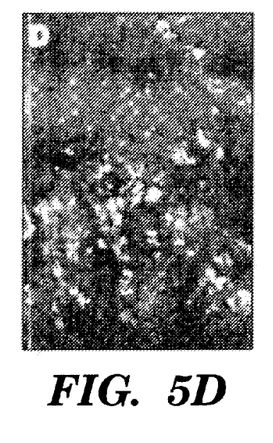
Figure 5E:
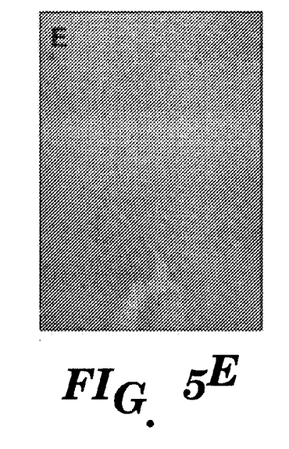
Figure 5F:
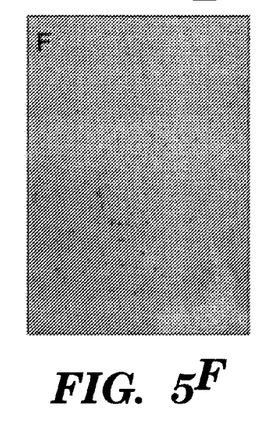
Figure 5G:
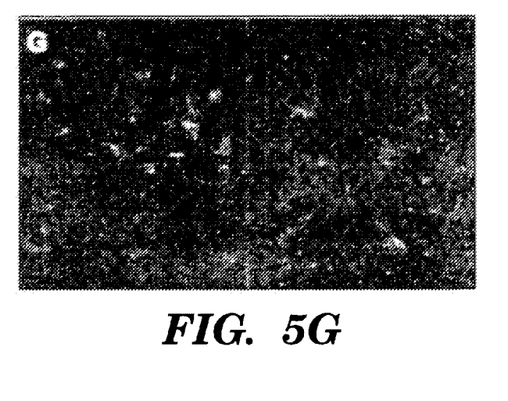

The CD gene provided an opportunity to examine a prototypical bioactive gene with a relevant, specific, quantifiable readout of functionality (oncolysis) that might be enhanced by tumor proximity. CD-bearing NSCs were first cocultured with glioma cells and when nearly confluent (FIG. 2A), exposed to 5-FC. Death of surrounding tumor cells was induced (FIG. 2B), even when the ratio of NSCs-to-tumor cells was as low as 1:4. NSCs that were mitotic at the time of 5-FC exposure self-eliminated. Control plates of tumor alone were not significantly killed by the same dose of 5-FC.

Example 3

+CD-Expressing NSCs Produce Anti-Tumor Effect in Vivo

On Day 0, adult nude mice received stereotactically guided injections into the right frontal lobe of CNS-1 glioblastoma alone ($7 \times 10^4$ in 2 µl PBS), or CNS-1 cells mixed with CD-NSCs ($7 \times 10^4$ CNS-1 and $3.5 \times 10^4$ NSCs in 2 µl PBS). Two days later treated animals received 10 intraperitoneal injections 900 mg/kg of 5-FC over a period of 10 days. Control animals received no 5-FC. Animals were sacrificed on day 13.

As shown in FIGS. 3A through 3D, animals receiving transplants of CD-NSCs and tumor cells followed by treatment with 5-FC, showed a significant reduction in tumor mass, as compared to the untreated animals.

Example 4

Intracerebral Tumor Implantation and Systemic NSC Administration

To determine if intravenous injection of neural stem cells would result in the cells targeting experimental intracerebral tumors, we conducted the following experiment: $1 \times 10^5$ CNS-1 glioma cells in 2 µl PBS were implanted into the right frontal lobe of adult nude mice. Seven days later, after the tumor was well established, $2 \times 10^6$ neural stem cells (C17.2) in 200 µl PBS were injected into the tail vein. The NSCs were given four days to distribute (potentially migrating out of the vasculature into the experimental tumor parenchyma, i.e., potentially crossing the blood-tumor barrier), after which the mice were sacrificed with anesthesia overdose. The brain, liver, kidneys, spleen, and heart were harvested and post-fixed overnight in 4% paraformaldehyde and then cryoprotected in 30% sucrose. Ten-micron serial cryostat sections were collected.

Brain tissue sections were stained with X-gal and Neutral Red to examine donor NSC distribution within the experimental intracranial tumor. X-gal staining revealed blue NSCs distributed throughout the tumor mass and not in surrounding normal appearing brain tissue. Double immunofluorescent staining with antibodies to β-galactosidase (to identify donor NSCs tumor) and tumor-specific antigens was also performed to provide independent confirmation of the presence of donor-derived cells within the tumor. The β-gal antibody immunofluorescent staining confirmed the X-gal results, that the NSCs were found in the tumor but not surrounding tissue. Staining such as this was not found in the absence of NSC injections or in NSC injected animal in the absence of tumor. Also, simply injecting vehicle rather than a tumor does not provide these findings.

Example 5

Extracerebral Tumor Implantation and Systemic NSC Administration

To determine if intravenous injection of neural stem cells would result in targeting of extracerebral tumors, we conducted the following experiment In the flank of an adult nude mouse, $3\text{-}4 \times 10^6$ CNS-1 rodent glioma or SH-SY5Y human neuroblastoma cells in 300 µl PBS were implanted subcutaneously. Three weeks later, the tumors were well established. Then, $2\text{-}3 \times 10^6$ neural stem cells in 200 µl PBS were injected into the tail vein. The neural stem cells were lacZ+murine NSCs (C17.2) or lacZ+murine NSCs retrovirally transduced with cytosine deaminase and selected with puromycin (C17.2 CD). The NSCs were given four days to circulate and potentially migrate out of and away from the vasculature into the experimental tumor tissue.

On the fourth day after tail vein NSC administration, the animals were sacrificed by anesthesia overdose. The tumor mass, liver, kidneys, spleen, heart and brain were harvested and post-fixed overnight in 4% paraformaldehyde and then cryoprotected in 30% sucrose. Ten-micron serial cryostat sections were collected.

Tumor tissue sections were stained with X-gal and neutral red to examine donor NSC within the experimental subcutaneous tumor mass. Four days after C17.2.CD cells were injected into the tail vein of a mouse with an established subcutaneous SH-SY5Y human neuroblastoma; X-gal staining revealed NSCs distributed throughout the tumor mass and not in surrounding tissue. After C17.2 cells were injected into the tail vein of a mouse with an established subcutaneous CNS-1 rat glioma, X-gal staining showed NSCs distributed throughout the tumor mass and not in surrounding tissue.

Immunofluorescent staining with antibodies to β-galactosidase (to identify NSCs) was performed to provide independent confirmation of the presence of donor-derived cells. The β-gal antibody immunofluorescent staining confirmed the X-gal results that the NSCs were found were found in the tumor. β-gal staining was not found in the absence of NSC injections or in NSC-injected animals in the absence of tumor.

Injecting vehicle alone, rather than NSCs, into the tumor did not provide these findings. In this example, injecting non-NSCs did not supply cells that left the vasculature and distributed themselves throughout the tumor.

From these findings we conclude that NSCs remained stably transfected with β-gal and that NSCs targeted extracranial/extraspinal tumors following intravascular administration (i.e. migrate out of the involved blood vessels to infiltrate the tumor). These cells do not further enlarge the tumor, over baseline.

This example has been repeated with different neural experimental tumors, including, but not limited to, rodent glioma (CNS-1/GFP), human glioma (HGL-21, U87, U251) and human neuroblastoma (SH-SY5Y). The tumor cells are conveniently injected subcutaneously into the flank of the recipient; however, other injection locations and methods known to those skilled in the art can be used as desired. A variety of stem cell lines can be used, preferably neural stem cells, including but not limted to murine NSCs or human NSCs. The NSCs are conveniently injected into the tail vein of the animal.

Example 6

Intravascularly Delivered CD-NSCs Display Tropism for Extracranial Tumors

As in the Example 5, an intravenous injection of cytosine deaminase-transduced NSCs was used to target an extracranial tumor, but harvested the tumor only 30 minutes following NSC injection. In the flank of an adult nude mouse, $4-5 \times 10^6$ SH-SY5Y human neuroblastoma cells in 300 μl PBS were implanted subcutaneously into the left and right flank. Three weeks later, the bilateral tumors were well established. At this point, the animal was anesthetized and the left tumor mass surgically removed, and skin closed. Then, $2-3 \times 10^6$ NSCs in 200 μl PBS were injected into the tail vein The NSCs were lacZ+murine NSCs retrovirally transduced with cytosine deaminase and selected with puromycin (C17.2.CD). The NSCs were given 30 minutes to circulate. The animal was sacrificed by anesthesia overdose and the right flank tumor mass surgically removed. Organs harvested included liver, kidneys, spleen, heart and brain which were post-fixed overnight with both tumor masses in 4% paraformaldehyde and then cryoprotected in 30% sucrose. Ten-micron serial cryostat sections were collected for histological analysis.

Figure 6A:
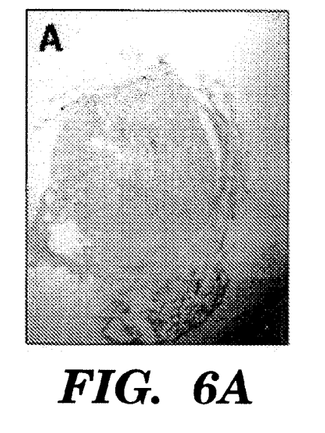
Figure 6B:
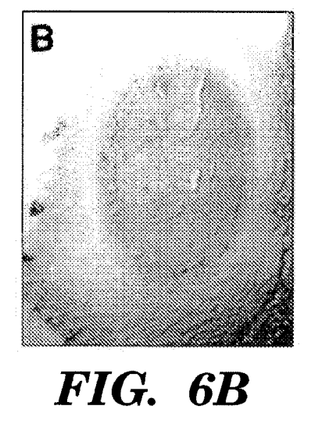
Figure 6C:
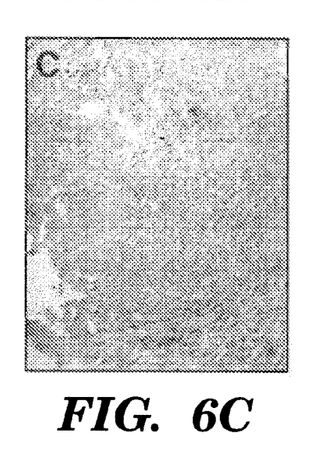
Figure 6D:
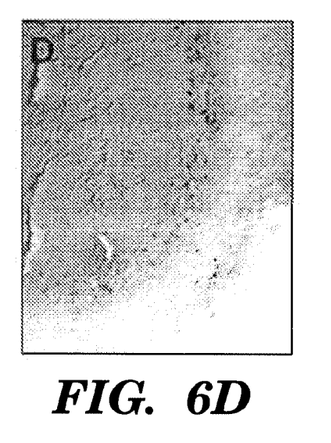
Figure 6E:
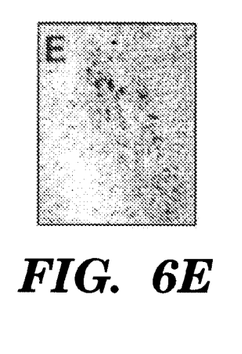
Figure 6F:
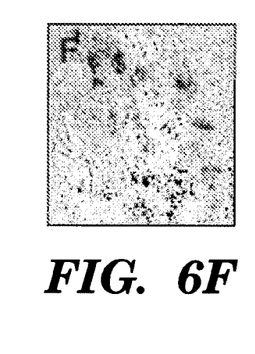
Figure 6G:
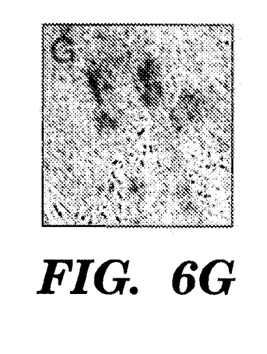

Tumor tissue sections were stained with X-gal and neutral red to examine donor NSC distribution within the experimental subcutaneous tumor mass. 30 minutes following C17.2.CD NSC injection into the tail vein of a mouse with an established right subcutaneous SH-SY5Y human neuroblastoma, X-gal staining revealed donor NSCs all along the outer portions of the tumor mass and not in surrounding, normal appearing tissue (FIG. 6B, D-G). No such staining was observed in the left SH-SY5Y tumor mass that was removed immediately prior to NSC injection (FIGS. 6A and 6C). Immunofluorescent staining with antibodies to β-galactosidase (to identify NSCS) was also performed to independently confirm the presence of donor-derived cells.

Example 7

Systemic NSC Treatment of Non-neural Extracranial Tumors

To determine if intravenous injection of neural stem cells would result in targeting of non-neural extracranial tumors, $10-12 \times 10^6$ human melanoma (SKBE) cells in 200 μl PBS were implanted subcutaneously in the flanks of adult nude mice, as in Example 5. After 2 weeks, $2-4 \times 10^6$ cytosine deaminase-transduced C17.CD2 murine NSCs were conveniently injected intravenously into the tail vein. The NSCs were given 30 minutes to circulate, followed-by animal sacrifice by asphyxiation. The tumor mass, liver, kidneys, spleen, heart and brain were harvested and postfixed overnight in 4% paraformaldehyde and then cryoprotected in 30% sucrose. Ten micron serial cryostat sections were collected. Tumor sections were stained with X-gal and neutral red to identify donor NSCs within the experimental tumor. After CD17.CD2 cells were injected into the tail vein of a mouse with an established subcutaneous melanoma, X-gal staining revealed NSCs distributed throughout the tumor mass, as in Examples 5 and 6.

Immunofluorescent staining with antibodies to β-galactosidase (to identify NSCs) was performed to provide independent confirmation of the presence of donor-derived cells. The β-gal antibody immunofluorescent staining confirmed the X-gal results that the NSCs were found in the tumor. β-gal staining was not found in the absence of NSC injections. Also, injecting vehicle alone, rather than NSCs, into the tumor did not provide these findings.

From these findings we conclude that systemically administered NSCs remained stably transfected and that NSCs targeted non-neural systemic tumors following intravascular administration. Even in non-neural tumors, the injected NSCs migrated out of the tumor vasculature to infiltrate the tumor parenchyma, without enlarging the tumor volume.

This example is repeated with different non-neural experimental tumors (both with and without the tendency to form metastases), including but not limited to human prostate cancer. As in Example 5, tumor cells are conveniently injected subcutaneously into the flank of the recipient, with other injection locations and methods used as desired. A variety of stem cell lines can be used preferably neural stem cells, including but not limited to murine NSCs or human NSCs. The NSCs are conveniently injected into the tail vein of the animal.

Example 8

Systemic NSC Treatment of Non-neural Extracranial Tumors

To determine if intravenous injection of neural stem cells would result in targeting of non-neural extracranial tumors, $10-12 \times 10^6$ human prostate carcinoma (PC3) cells in 200 μl PBS were implanted subcutaneously in the flanks of adult nude mice, as in Example 5. After 2 weeks, $1 \times 10^5$ cytosine deaminase-transduced C17.CD2 murine NSC's were conveniently injected directly into the subcutaneous tumor. The NSCs were given 3 days to distribute, followed by animal sacrifice by anesthesia overdose. The tumor mass, liver, kidneys, spleen, heart and brain were harvested and postfixed overnight in 4% paraformaldehyde and then cryoprotected in 30% sucrose. Ten micron serial cryostat sections were collected Tumor sections were stained with X-gal and neutral red to identify donor NSCs within the experimental tumor. After CD17.CD2 cells were injected directly into the established subcutaneous prostate carcinoma flank tumors of nude mice, X-gal staining revealed NSCs distributed throughout the tumor mass, as in Examples 5, 6 and 7.

Immunofluorescent staining with antibodies to β-galactosidase (to identify NSCs) was performed to provide independent confirmation of the presence of donor-derived cells. The β-gal antibody immunofluorescent staining confirmed the X-gal results that the NSCs were found in the tumor. As in Examples 5, 6 and 7, β-gal staining was not found in the absence of NSC injections and injecting vehicle alone rather than NSCs into the tumor did not provide these findings.

From these findings we conclude that NSCs directly injected into peripheral subcutaneous flank tumors remained stably transfected and that NSCs distributed themselves extensively throughout non-neural tumors, infiltrating the tumor parenchyma without enlarging the tumor volume. This example is repeated with different non-neural experimental tumors (both with and without the tendency to form metastases), including but not limited to human melanoma Tumor cells and NSCs are conveniently injected subcutaneously into the flank of the recipient, with other injection locations and methods used as desired. A variety of stem cell lines can be used preferably neural stem cells, including but not limited to murine NSCs or human NSCs.

Example 9

Systemic NSC Treatment of Extracranial Tumors

To determine if intravenous injection of neural stem cells would result in targeting of non-neural extracranial tumors, 2-5×106 human neuroblastoma (SH-SY5Y) cells in 200 μl PBS were implanted subcutaneously in the flanks of adult nude mice, as in Examples 5-8. After 3 weeks, 1-2×10$^6$ cytosine deaminase-transduced C17.CD2 murine NSC's were conveniently injected intravenously into the tail vein. The NSCs were given 3 days to circulate, followed by animal sacrifice by anesthesia overdose. The tumor mass, liver, kidneys, spleen, heart and brain were harvested and postfixed overnight in 4% paraformaldehyde and then cryoprotected in 30% sucrose. Ten micron serial cryostat sections were collected.

Tumor sections were stained with X-gal and neutral red to identity donor NSCs within the experimental tumor. After CD17.CD2 cells were injected directly into the established subcutaneous human neuroblastoma flank tumors of nude mice. X-gal staining revealed NSCs distributed throughout the tumor mass, as in Examples 5-8.

Horseradish peroxidase-Diaminobenzidine staining with antibodies to cytosine deaminase (to identify NSCs) was performed to provide independent confirmation of the presence of donor-derived cells. The cytosine deaminase staining confirmed the X-gal results that the NSCs were found in the tumor and were seen within the tumor vasculature, exiting out into the parenchyma. As in Examples 5, 6, 7, and 8, β-gal staining was not found in the absence of NSC injections and injecting vehicle alone rather than NSCs into the tumor did not provide these findings.

From these findings we conclude that NSCs intravascularly injected into the peripheral tail vein of nude mice bearing subcutaneous flank tumors remained stably transfected and that NSCs distributed themselves extensively throughout non-neural tumors, infiltrating the tumor parenchyma without enlarging the tumor volume.

What is claimed is:

1. A method for delivering a therapeutic substance encoded by a nucleic acid to the vicinity of tumor cells present in a human subject to inhibit tumor growth, said method comprising systemically administering using intravascular administration to said human genetically modified human subject neural stem cells expressing the therapeutic substance encoded by the nucleic acid, wherein said genetically modified human neural stem cells are capable of tracking the tumor cells and expressing the therapeutic substance encoded by the nucleic acid in the vicinity of the tumor cells to inhibit tumor growth, wherein the intravascular administration occurs at an extracranial site.

2. The method of claim 1, wherein the therapeutic substance encoded by the nucleic acid is an enzyme capable of converting a non-toxic compound to a toxic compound.

3. The method of claim 1, wherein the therapeutic substance encoded by the nucleic acid is a suicide gene.

4. The method of claim 1, wherein the genetically modified neural stem cells comprise a viral vector expressing the therapeutic substance encoded by the nucleic acid.

5. The method of claim 4, wherein the viral vector is a replication defective retroviral vector.

6. The method of claim 4, wherein the viral vector is a replication conditional herpes simplex viral vector.

7. The method of claim 1, wherein the tumor is a metastatic tumor.

8. The method of claim 1, wherein the tumor is an intracranial tumor.

9. The method of claim 1, wherein the tumor is an instraspinal tumor.

10. The method of claim 1, wherein the tumor is an extracranial tumor.

11. The method of claim 1, wherein the tumor is an extraspinal tumor.

* * * * *